(12) United States Patent
Smith et al.

(10) Patent No.: US 8,790,352 B2
(45) Date of Patent: Jul. 29, 2014

(54) OVOID TUNNEL GUIDE AND METHOD OF ACL RECONSTRUCTION

(75) Inventors: Graham Smith, Newburyport, MA (US); Alexander John Gutteridge, Hemingford Abbots (GB); James Richard Robinson, Chippenham (GB); Daniel B. Ellis, Holliston, MA (US)

(73) Assignee: Smith & Nephew, Inc., Memphis, TN (US)

(*) Notice: Subject to any disclaimer, the term of this patent is extended or adjusted under 35 U.S.C. 154(b) by 227 days.

(21) Appl. No.: 13/251,982

(22) Filed: Oct. 3, 2011

(65) Prior Publication Data
US 2013/0085503 A1    Apr. 4, 2013

(51) Int. Cl.
A61B 17/17    (2006.01)
A61F 2/08    (2006.01)

(52) U.S. Cl.
USPC .... 606/96; 623/13.11; 623/13.12; 623/13.14; 606/53; 606/54; 606/95

(58) Field of Classification Search
CPC .................................. A61F 2/08; A61B 17/17
USPC ........ 623/13.11–13.2; 606/59, 60, 79–80, 85, 606/232, 300–304, 53–54, 95–96
See application file for complete search history.

(56) References Cited

U.S. PATENT DOCUMENTS

| 5,152,790 | A  | * | 10/1992 | Rosenberg et al. | ........ 623/13.14 |
|---|---|---|---|---|---|
| 5,520,693 | A  |   | 5/1996  | McGuire et al. |   |
| 8,197,482 | B2 | * | 6/2012  | Stone | .............................. 606/80 |
| 2007/0191853 | A1 |   | 8/2007  | Stone |   |
| 2007/0233241 | A1 | * | 10/2007 | Graf et al. | .................. 623/13.14 |
| 2009/0018654 | A1 | * | 1/2009  | Schmieding et al. | ...... 623/13.14 |
| 2009/0163935 | A1 |   | 6/2009  | McCarthy et al. |   |
| 2010/0049201 | A1 |   | 2/2010  | Re |   |
| 2012/0059469 | A1 | * | 3/2012  | Myers et al. | ............... 623/13.14 |

OTHER PUBLICATIONS

International Search Report mailed Jan. 31, 2013 in corresponding International Application No. PCT/US2012/058563.

* cited by examiner

*Primary Examiner* — David Isabella
*Assistant Examiner* — Yashita Sharma
(74) *Attorney, Agent, or Firm* — Chapin IP Law, LLC

(57) ABSTRACT

A guide apparatus including a body having a proximal end, a distal end, a hole formed therethrough, and a central axis defined therethrough, and a projection member coupled to the distal end of the body. An outer diameter of the body is larger than an outer diameter of the projection member. Further, the projection member does not obstruct a pathway defined by the hole.

11 Claims, 6 Drawing Sheets

OVOID TUNNEL GUIDE AND METHOD OF ACL RECONSTRUCTION

BACKGROUND

Anterior cruciate ligament (ACL) re-construction techniques are applied to an increased number of re-construction operations. The ovoid morphology of the native tibial and femoral ACL attachment areas results in the ACL having a continuum of fibers whose length and tension changes differently with knee flexion.

Anteromedial (AM) bundle fibers have been shown to undergo small length changes from full extension to 90 degrees of flexion, whereas posterolateral (PL) bundle fibers demonstrate large changes in length from full extension to 90 degrees of flexion. The anteromedial and posterolateral bundles act synergistically to retrain anterior laxity through the range of knee flexion.

However, many surgeons have been reluctant to adopt double-bundle re-construction, citing concerns about accurate placement of multiple bone tunnels and femoral condoyle fracture as a result of weakness induced by multiple tunnels.

SUMMARY OF INVENTION

According to one aspect of the present invention, there is provided a guide apparatus including a body having a proximal end, a distal end, a hole formed therethrough, and a central axis defined therethrough, and a projection member coupled to the distal end of the body, in which an outer diameter of the body is larger than an outer diameter of the projection member, in which the projection member does not obstruct a pathway defined by the hole.

According to another aspect of the present invention, there is provided a method for ligament construction, the method including providing a guide configured to allow a drill to drill an oval-shaped tunnel within a bone, providing a fixation device having at least two separately-formed suture loops, in which a first graft and a second graft are coupled to the at least two suture loops, drilling an oval-shaped tunnel through a bone with the drill, using the guide, drawing the fixation device through the oval-shaped tunnel, orienting the first graft and the second graft within the oval-shaped tunnel, and securing the fixation device on an exterior surface of the bone.

DETAILED DESCRIPTION

The following is directed to various exemplary embodiments of the disclosure. Although one or more of these embodiments may be preferred, the embodiments disclosed should not be interpreted, or otherwise used, as limiting the scope of the disclosure, including the claims. In addition, those having ordinary skill in the art will appreciate that the following description has broad application, and the discussion of any embodiment is meant only to be exemplary of that embodiment, and not intended to suggest that the scope of the disclosure, including the claims, is limited to that embodiment.

Certain terms are used throughout the following description and claims refer to particular features or components. As those having ordinary skill in the art will appreciate, different persons may refer to the same feature or component by different names. This document does not intend to distinguish between components or features that differ in name but not function. The figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first component is coupled to a second component, that connection may be through a direct connection, or through an indirect connection via other components, devices, and connections. Further, the terms "axial" and "axially" generally mean along or substantially parallel to a central or longitudinal axis, while the terms "radial" and "radially" generally mean perpendicular to a central, longitudinal axis.

As many surgeons have been reluctant to adopt double-bundle re-construction, citing concerns about accurate placement of multiple bone tunnels and femoral condoyle fracture as a result of weakness induced by multiple tunnels, embodiments disclosed herein relate to guides and methods that may be used with a fixation device to help perform ligament re-construction, with one or more separate grafts, and may be utilized in a single bone tunnel.

Figure 1:
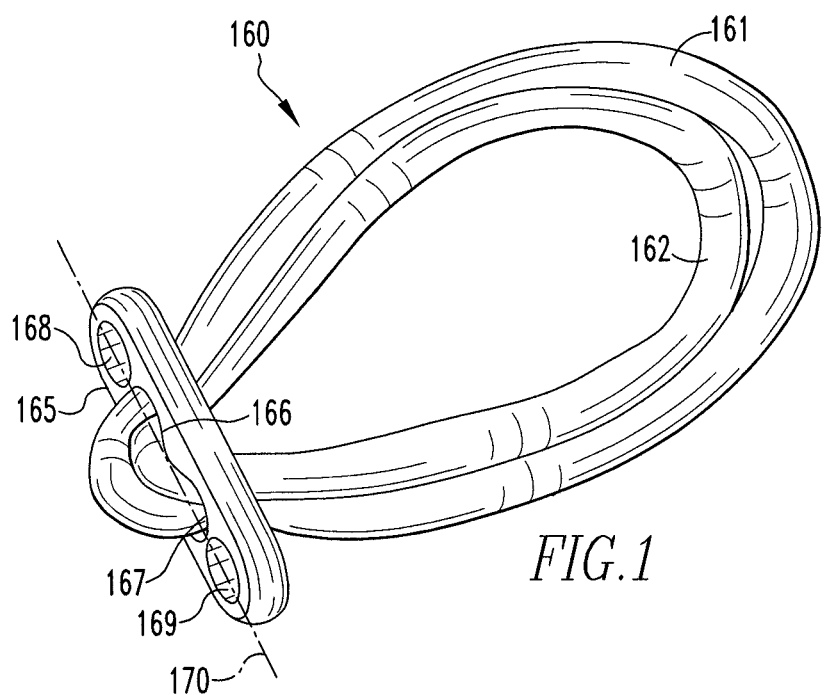
FIG. 1 is a perspective view of a graft attachment apparatus, according to embodiments disclosed herein.

Referring to FIG. 1, a graft attachment apparatus 160, according to embodiments disclosed herein, is shown. In one or more embodiments, the graft attachment apparatus 160 may include at least two filament loops 161, 162 and a fixation member 165. In one or more embodiments, the at least two filament loops 161, 162 may be a first filament loop 161 and a second filament loop 162.

In one or more embodiments, the at least two filament loops 161, 162 may be separately formed. As shown, each of the first filament loop 161 and the second filament loop 162 are separately formed loops. In other words, the first filament loop 161 is not connected to, and is not a part of, the second filament loop 162.

Further, in one or more embodiments, the at least two filament loops 161, 162 may be continuous loops. In other words, in one or more embodiments, each of the first filament loop 161 and the second filament loop 162 may be continuous loops. As shown in FIG. 1, each of the first filament loop 161 and the second filament loop 162 are continuous loops. In other words, each of the first filament loop 161 and the second filament loop 162 are closed loops that are not tied, or knotted, loops. For example, as shown, neither the first filament loop 161 nor the second filament loop 162 is a loop which is knotted. Instead, each of the first filament loop 161 and the second filament loop 162 are continuous loops, which are closed loops that are closed without the use of knots.

In one or more embodiments, the at least two filament loops 161, 162 may be at least two separately formed suture loops. In other words, in one or more embodiments, each of the first filament loop 161 and the second filament loop 162 may be separately formed suture loops. However, those having ordinary skill in the art will appreciate that the at least two filament loops 161, 162 may be formed from any material known in the art. For example, in one or more embodiments, each of the first filament loop 161 and the second filament loop 162 may be formed from a continuous loop of polyester, suture, or polyester closure tape.

Further, in one or more embodiments, the at least two separately formed filament loops 161, 162 may be different in length. In other words, a length of the first filament loop 161 may be different from a length of the second filament loop 162. In one or more embodiments, the first filament loop 161 may have a length of 15 mm, and the second filament loop 162 may have a length of 20 mm. However, those having ordinary skill in the art will appreciate that each of the first filament loop 161 and the second filament loop 162 may be of any length. For example, in one or more embodiments, the first filament loop 161 may have a length of 20 mm, and the second filament loop 162 may have a length of 15 mm. Further, in one or more embodiments, both the first filament loop 161 and the second filament loop 162 may have equal lengths. Furthermore, in one or more embodiments, each of the first filament loop 161 and the second filament loop 162 may be of any length smaller or larger than 15 mm or 20 mm. In one or more embodiments, the length of the first filament loop 161 and the second filament loop 162 may be dependent on the dimensions, or the type of, graft that may be coupled to each of the first filament loop 161 and the second filament loop 162.

In one or more embodiments, the at least two separately formed filament loops 161, 162 may be configured to be coupled, or attached, to separate grafts or ligaments, e.g., anteromedial and posterolateral fiber bundles. However, those having ordinary skill in the art will appreciate that each of the first filament loop 161 and the second filament loop 162 may be configured to be coupled, or attached, to any other grafts known in the art.

As discussed above, in one or more embodiments, the graft attachment apparatus 160 may include the fixation member 165, the fixation member 165 having a longitudinal axis 170 defined therethrough. In one or more embodiments, the fixation member 165 may include at least one opening configured to receive the at least two separately formed suture loops 161, 162. In other words, in one or more embodiments, the fixation member 165 may include at least one opening configured to receive each of the first filament loop 161 and the second filament loop 162. In one or more embodiments, the fixation member 165 may include a single opening, configured to receive both the first filament loop 161 and the second filament loop 162. Alternatively, in one or more embodiments, the fixation member 165 may include a first opening 166 configured to receive the first filament loop 161 and a second opening 167 configured to receive the second filament loop 162. Further, as shown in FIG. 1, in one or more embodiments, the fixation member 165 may include the first opening 166 and the second opening 167, in which both the first opening 166 and the second opening 167 are configured to receive both the first filament loop 161 and the second filament loop 162.

Those having ordinary skill in the art will appreciate that more openings may be formed in, i.e., through, the fixation member 165 than described above. For example, in one or more embodiments, the fixation member 165 may include a third opening 168 configured to receive a lead filament (not shown) and a fourth opening 169 configured to receive a trailing filament, i.e., a flip suture (not shown). In one or more embodiments, the third opening 168 and the fourth opening 169 may be formed on opposite sides of the fixation member 165 with the first opening 166 and the second opening 167 formed between the third opening 168 and the fourth opening 169. Alternatively, the third opening 168 and the fourth opening 169 may be formed on opposite sides of the fixation member 165 with a single opening configured to receive both the first filament loop 161 and the second filament loop 162, discussed above, formed between the third opening 168 and the fourth opening 169.

In one or more embodiments, the fixation member 165 may be formed from a biocompatible material. For example, in one or more embodiments, the fixation member 165 may be formed from a biocompatible material such as titanium or acetal. Alternatively, in one or more embodiments, the fixation member 165 may be formed from, or with, a bioabsorbable material such as polylactic acid or polyglycolic acid.

Furthermore, in one or more embodiments, the fixation member 165 may be elongate, or oblong, in shape. In other words, in one or more embodiments, a length of the fixation member 165 may be larger than a width of the fixation member 165. As shown in FIG. 1, the fixation member 165 is elongate, or oblong, in shape. As such, the fixation member may be received within a tunnel (not shown), in which a diameter of the tunnel is larger than the width of the fixation member 165, but is smaller than the length of the fixation member 165. Accordingly, in one or more embodiments, the fixation member 165 may be disposed within the tunnel, substantially along the longitudinal axis 170 of the fixation member 165. Once the fixation member 165 exits the tunnel, the fixation member 165 may be secured on the other side of the tunnel, e.g., the fixation member 165 may prevent itself from entering back into the tunnel, by being re-oriented such that the longitudinal axis 170 of the fixation member 165 is substantially perpendicular to the tunnel. In other words, because the length of the fixation member 165 is larger than the diameter of the tunnel, the fixation member 165 may prevent itself from entering back into the tunnel by orienting itself such that the length of the fixation member 165 is disposed across the diameter of the tunnel.

Figure 2A:
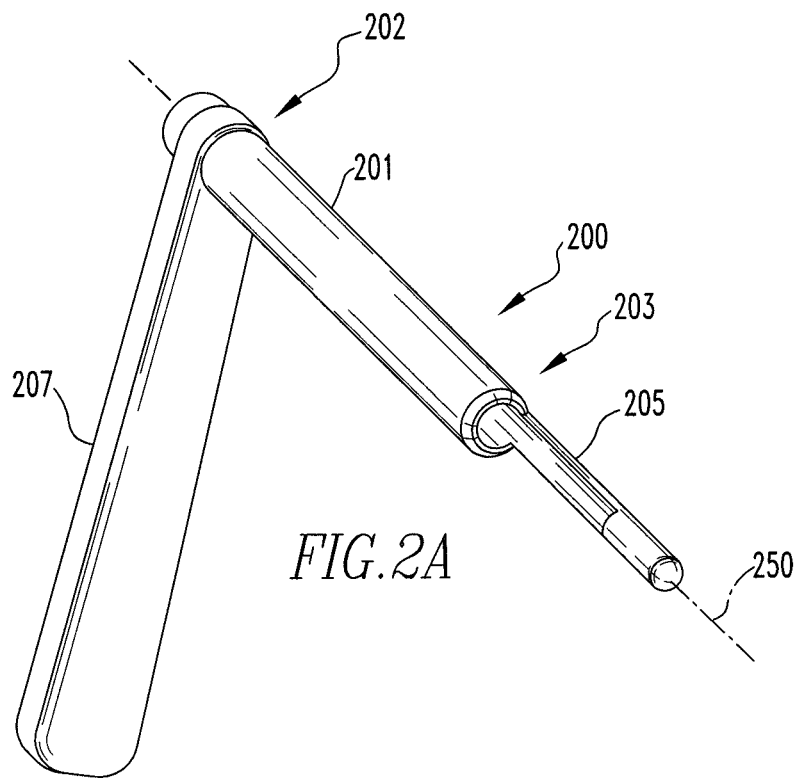
FIGS. 2A-2B are multiple views of a guide, according to embodiments disclosed herein.
Figure 2B:
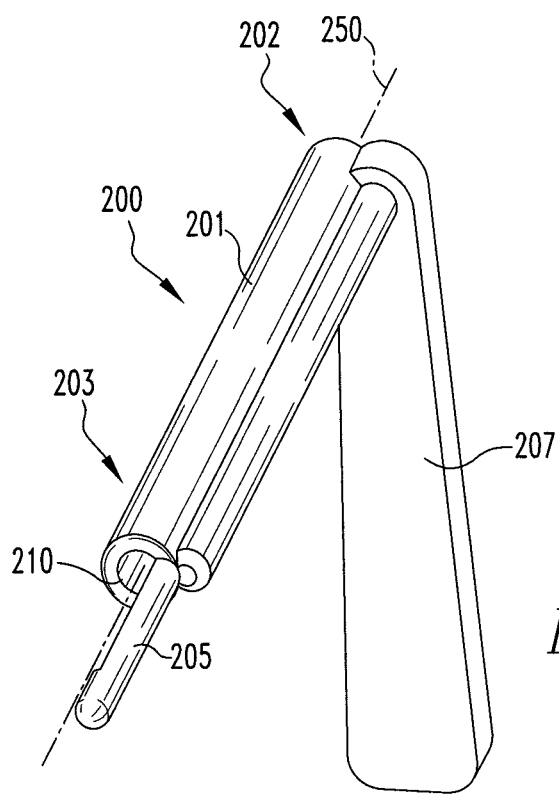

Referring to FIGS. 2A and 2B, multiple views of a guide 200 are shown. In one or more embodiments, the guide 200 may include a body 201 having a proximal end 202, a distal end 203, a hole 210 formed therethrough, and a central axis 250 defined therethrough. In one of more embodiments, the hole 210 may be formed along the central axis 250. Alternatively, in one or more embodiments, the hole 210 may be formed in a direction that is substantially parallel with the central axis 250, but may be off-set from the central axis 250. Further, in one or more embodiments, a projection member 205 may be coupled to a distal end 203 of the body 201.

In one or more embodiments, an outer diameter of the body 201 of the guide 200 may be larger than an outer diameter of the projection member 205. For example, as shown, an outer diameter of the body 201 is larger than an outer diameter of the projection member 205. In other words, in one or more embodiments, the diameter of the projection member 205 may be smaller, or less than, the diameter of the body 201.

In one or more embodiments, the hole 210 may be configured to receive, at least a portion of, a drill, a drilling apparatus, or a drilling device. Those having ordinary skill in the art will appreciate that, as used herein, a drill, drilling apparatus, or drilling device may be any apparatus or device that is capable of forming a hole in a surface, e.g., a bone.

In one or more embodiments, the hole 210 may be formed through the body 201 in a direction that is substantially parallel to the central axis 250 of the body 201. For example, in one or more embodiments, the hole 210 may be formed along the central axis 250 of the body 201. Alternatively, in one or more embodiments, a central axis of the hole 210 is offset from the central axis 250 of the body 201. In other words, in one more embodiments, the hole 210 may be formed in a direction that is parallel to the central axis 250, but may be offset from the central axis 250 such that the hole 210 is not centered about the central axis 250 of the body 201.

Further, in one or more embodiments, the projection member 205 may not obstruct a pathway defined by the hole 210. In one or more embodiments, a pathway defined by the hole 210 may be a extension of a diameter of the hole 210, extended beyond the hole 210. For example, an object, e.g., a drill, that is disposed into the hole 210 and exits the hole 210 may occupy a pathway defined by the hole 210. In one or more embodiments, the pathway defined by the hole 210 may be adjacent to the projection member 205 such that the projection member 205 does not cover any portion of the hole 210 or a pathway defined by a diameter of the hole 210. In other words, in one or more embodiments, the outer diameter of the projection member 205 may not interfere, or overlap with, the hole 210. As such, in one or more embodiments, an object, e.g., a drill, may be disposed through the hole 210 of the guide 200 without interference from the projection member 205. Alternatively, in one or more embodiments, a portion of the projection member 205 may overlap with, or interfere with, a pathway defined by the diameter of the hole 210.

As shown in FIGS. 2A and 2B, in one or more embodiments, the guide 200 may include a handle 207 coupled to the proximal end 202 of the body 201. The handle 207 may be formed from any substantially rigid, or substantially flexible, material known in the art, such as metal, plastic, or polymer known in the art. In one or more embodiments, the handle 207 may be coupled to the body 201 at an angle that is between 1 and 90 degrees from the central axis 250 of the body 201. For example, as shown in FIGS. 2A and 2B, the handle 207 may be coupled to the proximal end 202 of the body 201 at an angle that is substantially 90 degrees from the central axis 250 of the body 201.

However, in one or more embodiments, the handle 207 may be coupled to the proximal end 202 of the body 201 at an angle that is more than, or less than, 90 degrees from the central axis 250 of the body 201. For example, in one or more embodiments, the handle 207 may be coupled to the proximal end 202 of the body 201 at a 1 degree angle from the central axis 250 of the body 201, such that the handle 207 extends 1 degree from a vertical direction, away from the body 201. Alternatively, in one or more embodiments, the handle 207 may be coupled to the proximal end 202 of the body 201 at a 1 degree angle from the central axis 250 of the body 201, such that the handle 207 extends 1 degree from a vertical direction, substantially against the body 201. In other words, in one or more embodiments, the handle 207 may be coupled to the proximal end 202 of the body 201 at an angle that is more than, or less than, 90 degrees from the central axis 250 of the body 201, and may extend either toward or away from the distal end 203 of the body 201.

The guide 200 may be formed from any substantially rigid, or substantially flexible, material known in the art. For example, in one or more embodiments, the guide 200 may be formed from any metal, plastic, or polymer known in the art, such as steel or any biocompatible polymer.

According to another aspect, there is provided a method for ligament construction. The method may include providing a guide configured to allow a drill to drill an oval-shaped tunnel within a bone, providing a fixation device having at least two separately-formed suture loops, in which a first graft and a second graft are coupled to the at least two suture loops, drilling an oval-shaped tunnel through a bone with the drill, using the guide, drawing the fixation device through the oval-shaped tunnel, orienting the first graft and the second graft within the oval-shaped tunnel, and securing the fixation device on an exterior surface of the bone.

As discussed above, according to one or more aspects, the guide may include a body having a proximal end, a distal end, a hole formed therethrough, and a central axis defined therethrough, and a projection member coupled to the distal end of the body.

According to one or more aspects, drilling an oval-shaped tunnel through a bone with the drill, using the guide, may include drilling a central tunnel into the bone, disposing at least a portion of the guide into the central tunnel formed in the bone, disposing the drill within the hole formed through the guide, drilling a first tunnel into the bone, drilling a second tunnel into the bone, in which the first tunnel overlaps the second tunnel.

According to one or more aspects, disposing at least a portion of the guide into the central tunnel formed in the bone may include disposing at least a portion of the projection member of the guide into the central tunnel formed in the bone. The method may also include pivoting the guide about the projection member between a first position and a second position.

Figure 3A:
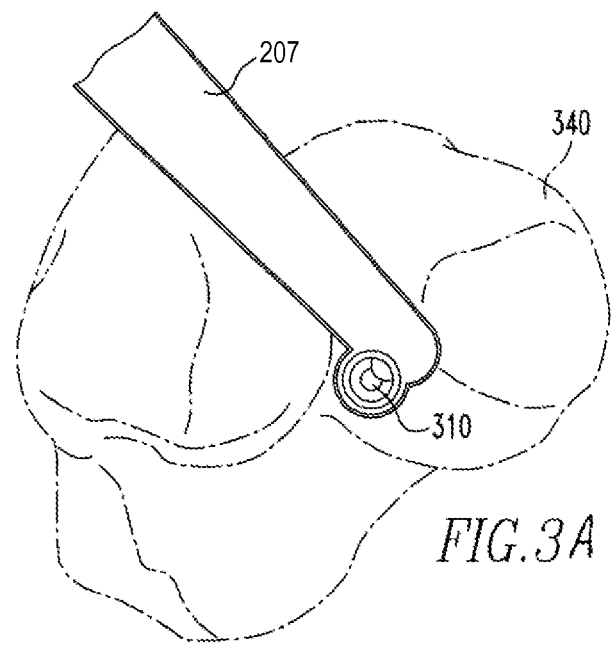
FIG. 3A is a top view of a guide in a first position, engaged with a bone, according to embodiments disclosed herein.
Figure 3B:
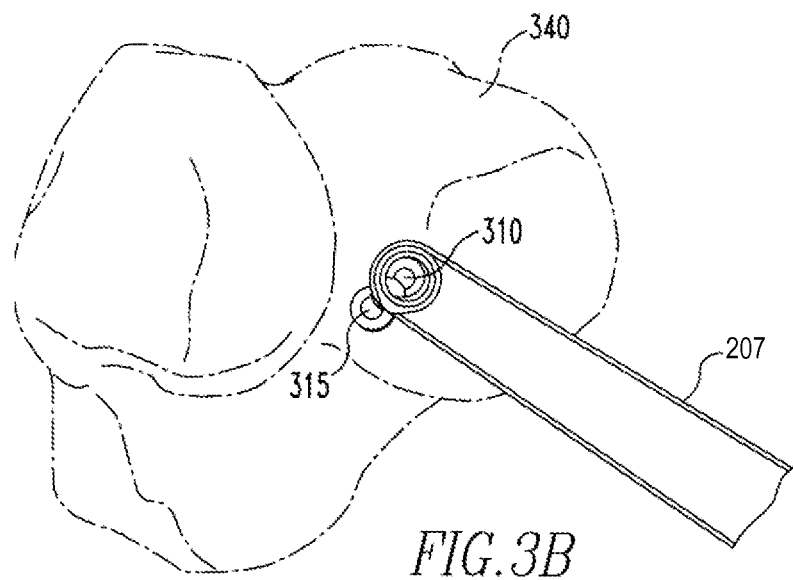
FIG. 3B is a top view of a guide in a second position, engaged with a bone, according to embodiments disclosed herein.

For example, referring to FIGS. 3A and 3B, top views of a guide 300 in a first position and a second position are shown, respectively, in accordance with embodiments disclosed herein. As shown in FIG. 3A, a projection member (not shown) of the guide 300 may be disposed in a central hole (not shown) formed in a bone 340. As such, according to one or more aspects, the guide 300 may be configured to pivot about the projection member that is disposed in the central hole formed in the bone 340. As shown in FIG. 3A, the guide 300 is in a first position, in which a hole 310, formed through a body of the guide 300, is positioned over an exterior surface of the bone 340 to guide a drill configured to drill, or form, a tunnel in the bone 340. In other words, as shown in FIG. 3A, in the first position, the hole 310 of the guide 300 is configured to guide a drill to form a first tunnel in the bone 340 along a pathway defined by the hole 310. As discussed above, a pathway defined by the hole 310 may be a extension of a diameter of the hole 310, extended beyond the hole 310, e.g., into the bone 340.

As shown in FIG. 3B, a first tunnel 315 is formed in the bone 340. Further, as shown, the guide 300 is in a second position, in which the hole 310, formed through the body of the guide 300, is positioned over an exterior surface of the bone 340 to guide a drill configured to drill, or form, a second tunnel in the bone 340. According to one or more aspects, the second position of the guide 300 may be any position that is not the first position of the guide 300. For example, once the first tunnel 315 is formed in the bone 340, the guide 300 may be pivoted, or rotated, about the projection member of the guide 300, between 1 degree and 359 degrees to arrive at the second position. According to one or more aspects, the second position of the guide 300 may involve rotation of the guide 300 substantially 180 degrees from the first position. Alternatively, according to one or more aspects, the second position of the guide 300 may involve rotation of the guide 300 substantially 60 degrees from the first position. Subsequently, a second tunnel (not shown) may be formed in the bone 340 with the drill along a pathway defined by the hole 310.

According to one or more aspects, the central tunnel, into which the projection member of the guide 300 may be disposed, the first tunnel 315, and the second tunnel (not shown) may be overlapping tunnels. For example, according to one or more aspects, each of the first tunnel 315 and the second tunnel may overlap, at least a portion of, the central tunnel. Accordingly, such a configuration may result in an oval-shaped tunnel, an oblong tunnel, and/or an elongate tunnel. Alternatively, according to one or more aspects, the first tunnel 315 may overlap with both the central tunnel and the second tunnel. Accordingly, such a configuration may result in a triangular-shaped tunnel. Those having ordinary skill in the art will appreciate that, as used herein, an oval-shaped tunnel may refer to, and include, an oblong tunnel, an elongate tunnel, an elliptically-shaped tunnel, a V-shaped tunnel, a chevron-shaped tunnel, an L-shaped tunnel, and a triangular-shaped tunnel.

Further, according to one or more aspects, the oval-shaped tunnel may be a tunnel of any shape that is configured to receive a fixation device, as described above, but may also allow the fixation device to be oriented to prevent the fixation device from being disposed into the oval-shaped tunnel. Further, those having ordinary skill in the art will appreciate that the oval-shaped tunnel may be formed completely through a bone, e.g., a tibia and/or a femur. Alternatively, according to one or more aspects, the oval-shaped tunnel may not necessarily be formed completely through the bone 340.

Figure 4A:
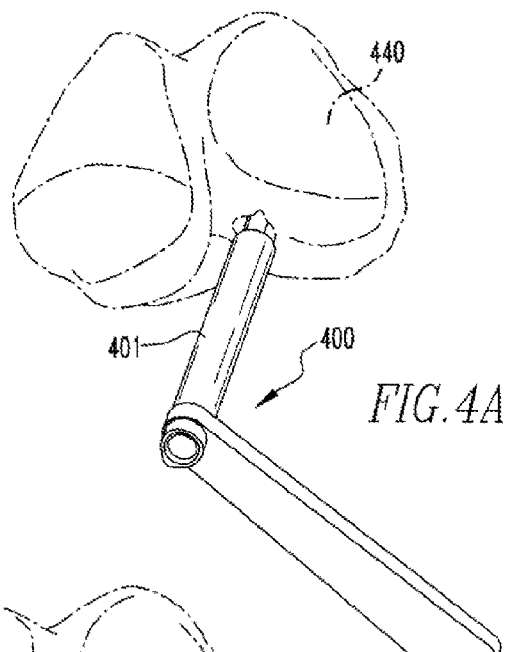
FIGS. 4A-4C are multiple schematic views of a guide engaged with a bone, according to embodiments disclosed herein.
Figure 4B:
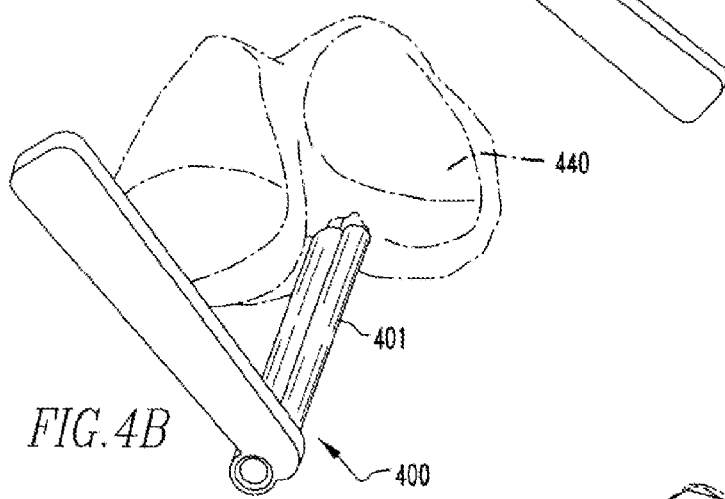
Figure 4C:
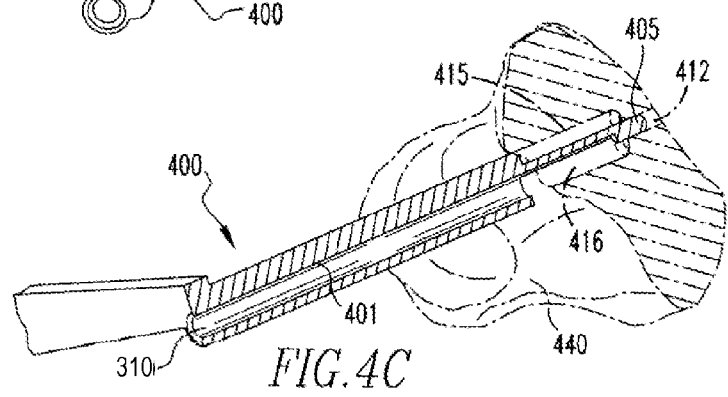

Referring to FIGS. 4A-4C, multiple views of a guide 400 engaged with a bone 440, in accordance with embodiments disclosed herein, are shown. According to one or more aspects, the guide 400 may include a body 401 and a projection member 405.

As discussed above, a central tunnel 412 may be formed in the bone 440. According to one or more aspects, the central tunnel 412 may be formed using a drill, a drilling apparatus, or a drilling device. According to one or more aspects, the central tunnel 412 may be configured to receive, at least a portion of, the projection member 405 of the guide 400. Further, according to one or more aspects, once at least a portion of the projection member 405 is received within the central tunnel 412, the guide 400 may be configured to rotate about the projection member 405 between a first position and a second position, as discussed above.

Further, as discussed above, those having ordinary skill in the art will appreciate that, as used herein, a drill, drilling apparatus, or drilling device may be any apparatus or device that is capable of forming a hole in a surface, e.g., the bone 440.

As shown in FIG. 4A, the guide 400 may be engaged with the bone 440 in the first position, as described above. As discussed above, in the first position, the guide 400 may be positioned to allow a drill to be disposed within hole (not shown) formed through the body 401 of the guide 400, in which the drill may be configured to form a tunnel in the bone 440, e.g., a first tunnel 415. According to one or more aspects, once the first tunnel 415 is formed in the bone 440, the guide 400 may be pivoted, or rotated, into the second position.

As shown in FIG. 4B, the guide 400 may be engaged with the bone 440 in the second position, as described above. Further, as discussed above, according to one or more aspects, the second position of the guide 400 may be any position that is not the first position of the guide 400. For example, once the first tunnel 415 is formed in the bone 440, the guide 400 may be pivoted, or rotated, about the projection member 405 of the guide 400, between 1 degree and 359 degrees to arrive at the second position. According to one or more aspects, the second position of the guide 400 may involve rotation of the guide 400 substantially 180 degrees from the first position. Alternatively, according to one or more aspects, the second position of the guide 400 may involve rotation of the guide 400 substantially 60 degrees from the first position. Subsequently, a second tunnel 416 may be formed in the bone 440 with the drill along a pathway defined by the hole (not shown).

According to one or more aspects, once the guide 400 is in the second position, the guide 400 may be used to allow a drill to be disposed within hole (not shown) formed through the body 401 of the guide 400, in which the drill may be configured to form a tunnel in the bone 440, e.g., the second tunnel 416.

Referring to FIG. 4C, the guide 400 is shown engaged with the bone, e.g., at least a portion of the projection member 405 is disposed, or received within, the central tunnel 412. Further, as shown, the first tunnel 415 and the second tunnel 416 are formed on opposite sides of the central tunnel 412. As discussed above, the position of the second tunnel 416, relative to the first tunnel 415, may be formed at any position that is not the first position. In other words, the second position of the guide 400 may be any position that is not the first position of the guide 400. As such, the second tunnel 416, which is formed based on the second position of the guide 400, may be formed at any position in the bone that is exactly where the first tunnel 415 is formed. However, as discussed above, according to one or more aspects, the first tunnel 415 and the second tunnel 416 may overlap.

As discussed above, according to one or more aspects, the central tunnel 412, into which the projection member 405 of the guide 400 may be disposed, the first tunnel 415, and the second tunnel 416 may be overlapping tunnels. For example, according to one or more aspects, each of the first tunnel 415 and the second tunnel 416 may overlap, at least a portion of, the central tunnel 412. Accordingly, such a configuration may result in an oval-shaped tunnel, an oblong tunnel, and/or an elongate tunnel. Alternatively, according to one or more aspects, the first tunnel 415 may overlap with both the central tunnel 412 and the second tunnel 416. Accordingly, such a configuration may result in a triangular-shaped tunnel. Those having ordinary skill in the art will appreciate that, as used herein, an oval-shaped tunnel may refer to, and include, an oblong tunnel, an elongate tunnel, an elliptically-shaped tunnel, a V-shaped tunnel, a chevron-shaped tunnel, an L-shaped tunnel, and a triangular-shaped tunnel.

According to one or more aspects, a depth of the central tunnel 412 may be larger than a depth of the first tunnel 415 and the second tunnel 416. However, those having ordinary skill in the art will appreciate that the depth of the central tunnel 412 may not necessarily be larger than a depth of the first tunnel 415 and the second tunnel 416. For example, according to one or more aspects, the depth of the first tunnel 415 may be larger than both the depth of the central tunnel 412 and the second tunnel 416. Alternatively, according to one or more aspects, the depth of the first tunnel 415 may be equal to the depth of the second tunnel 416, and the depth of the central tunnel 412 may be smaller or larger than the depths of the first tunnel 415 and the second tunnel 416. Furthermore, according to one more aspects, the depths of each of the central tunnel 412, the first tunnel 415, and the second tunnel 416 may all be equal depths. For example, according to one or more aspects, each of the central tunnel 412, the first tunnel 415, and the second tunnel 416 may be formed completely through the bone 440.

Figure 5A:
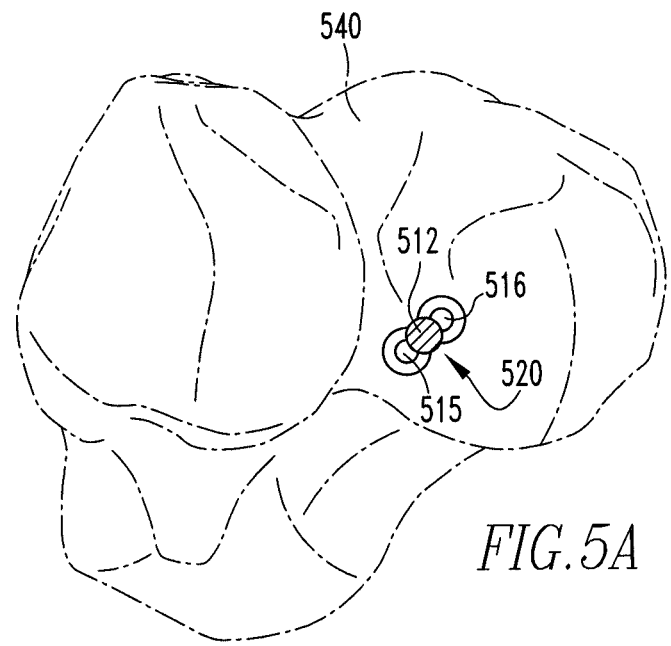
FIGS. 5A-5B are multiple schematic views of an oval-shaped tunnel formed using a guide, according to embodiments disclosed herein.
Figure 5B:
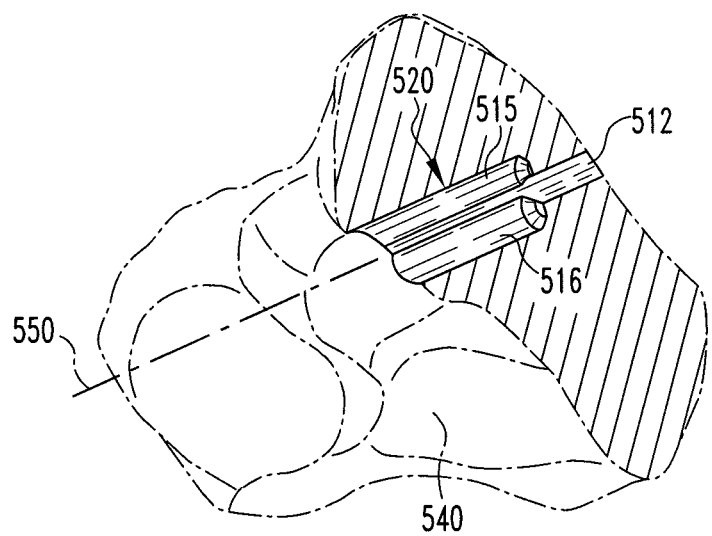

Referring to FIGS. 5A and 5B, multiple views of an oval-shaped tunnel 520 formed in a bone 540 having a longitudinal axis 550, formed using a guide (not shown), e.g., the guide 400 shown in FIGS. 4A-4C, in accordance with embodiments disclosed herein, are shown. As shown, a central tunnel 512, a first tunnel 515, and a second tunnel 516 may be overlapping tunnels, and may form the oval-shaped tunnel 520 in the bone 540. As will be discussed below, the oval-shaped tunnel 520 may be configured to receive a fixation device, in which a first graft and a second graft may be coupled to the fixation device.

As discussed above, according to one or more aspects, the first tunnel 515 may overlap with both the central tunnel 512 and the second tunnel 516. Accordingly, such a configuration may result in a triangular-shaped tunnel. Those having ordinary skill in the art will appreciate that, as used herein, an oval-shaped tunnel may refer to, and include, an oblong tunnel, an elongate tunnel, an elliptically-shaped tunnel, a V-shaped tunnel, a chevron-shaped tunnel, an L-shaped tunnel, and a triangular-shaped tunnel.

According to one or more aspects, the bone may be a tibia and/or a femur. However, those having ordinary skill in the art will appreciate that the bone may be any bone in a body, and may not be limited to only a tibia and/or a femur. For example, according to one or more aspects, the bone may be a humerus.

Further, according to one or more aspects, a lead suture may be coupled to the fixation device and the lead suture may be used to draw the fixation device through the oval-shaped tunnel. In other words, drawing the fixation device through the oval-shaped tunnel may include drawing the fixation device through the oval-shaped tunnel with the lead suture.

For example, according to one or more aspects, once a fixation device is disposed within an oval-shaped tunnel, e.g., the oval-shaped tunnel 520 shown in FIGS. 5A and 5B, a lead suture coupled to the fixation device may be used to draw, or pull, the fixation device through the oval-shaped tunnel.

According to one or more aspects, a flip suture may be coupled to the fixation device. As will be discussed below, the flip suture may be used, or manipulated, to assist with the re-orientation of the fixation device on a surface of the bone.

According to one or more aspects, the method may also include orienting the fixation device within the oval-shaped tunnel, in which orienting the fixation device within the oval-shaped tunnel may include substantially aligning a longitudinal axis of the fixation device with a longitudinal axis of the oval-shaped tunnel.

For example, according to one or more aspects, once a fixation device is disposed within an oval-shaped tunnel, e.g., the oval tunnel 520 shown in FIGS. 5A and 5B, the fixation device may be oriented within the oval-shaped tunnel such that a longitudinal axis of the fixation device may be substantially aligned with a longitudinal axis of the oval-shaped tunnel, e.g., the longitudinal axis 550 of the oval-shaped tunnel 520 shown in FIGS. 5A and 5B. Such an orientation may allow an oval-shaped tunnel of a minimal diameter, e.g., a diameter that may be only slightly larger than a width of the fixation device. As such, a diameter of the oval-shaped tunnel may be minimized, while still allowing the fixation device to be drawn, or pulled, through the oval-shaped tunnel. With the fixation device oriented such that the longitudinal axis of the fixation device is substantially aligned with the longitudinal axis of the oval-shaped tunnel, the diameter of the oval-shaped tunnel may only need to be slightly larger than the width of the fixation device in order to allow the fixation device to be received within the oval-shaped tunnel and be drawn, or pulled, through the oval-shaped tunnel, e.g., by a lead suture, as described above.

According to one or more aspects, orienting the first graft and the second graft within the oval-shaped tunnel may include turning, twisting, or otherwise re-orienting the fixation device within the oval-shaped tunnel such that the first graft and the second graft, which may be coupled to a first suture loop and a second suture loop of the fixation device, respectively, are aligned as desired. For example, as described above, an AM bundle and a PL bundle may have different characteristics.

As such, it may be advantageous, for recovery purposes, to orient the AM bundle and the PL bundle within the oval-shaped tunnel in a pre-determined orientation. For example, according to one or more aspects, it may be advantageous to place the AM bundle near an anterior region, and medially, in the tibia, and close to the "over the top" position in the femur. In other words, according to one or more aspects, it may be advantageous, both anatomically and physiologically, to place the AM bundle and the PL bundle in a pre-determined orientation within the oval-shaped tunnel by manipulating the fixation device to more closely reproduce the native ACL, without having to drill additional tunnels within the bone. According to one or more aspects, this may be accomplished by turning, twisting, or otherwise re-orienting the fixation device within the oval-shaped tunnel such that the AM bundle and the PL bundle are aligned in the pre-determined orientation.

According to one or more aspects, securing the fixation device on an exterior surface of the bone may include re-orienting the fixation device such that the longitudinal axis of the fixation device may be substantially perpendicular to the longitudinal axis of the oval-shaped tunnel.

As discussed above, a diameter of the oval-shaped tunnel may be minimized, while still allowing the fixation device to be received within, and be drawn through the oval-shaped tunnel. For example, according to one or more aspects, and as discussed above, the diameter of the oval-shaped tunnel may only need to be slightly larger than the width of the fixation device in order to allow the fixation device to be received within the oval-shaped tunnel and be drawn, or pulled, through the oval-shaped tunnel. Subsequently, once the fixation device is drawn through the oval-shaped tunnel, and exits the oval-shaped tunnel, the fixation device may be re-oriented to prevent the fixation device from being disposed into the oval-shaped tunnel, i.e., retain the fixation device on a surface of the bone.

For example, a fixation device may be disposed through an oval-shaped tunnel, e.g., the oval-shaped tunnel 520 shown in FIGS. 5A and 5B, and may exit the oval-shaped tunnel. Further, the fixation device may be re-oriented such that a longitudinal axis of the fixation device is substantially perpendicular to a longitudinal axis of the oval-shaped tunnel, e.g., the longitudinal axis 550 of the oval-shaped tunnel 520 shown in FIGS. 5A and 5B. As such, this orientation of the fixation device may be such that a length of fixation device, which may be greater than the width of the fixation device, may be disposed across an entrance of the oval-shaped tunnel on the surface of the bone. Accordingly, as the length of the fixation device may be greater than the width of the fixation device, such an orientation of the fixation device may prevent the fixation device from being disposed into the oval-shape tunnel, and may retain the fixation device on a surface of the bone.

According to one or more aspects, re-orienting the fixation device such that a longitudinal axis of the fixation device is substantially perpendicular to a longitudinal axis of the oval-shaped tunnel includes manipulating the flip suture to re-orient the fixation device on the bone.

Figure 6:
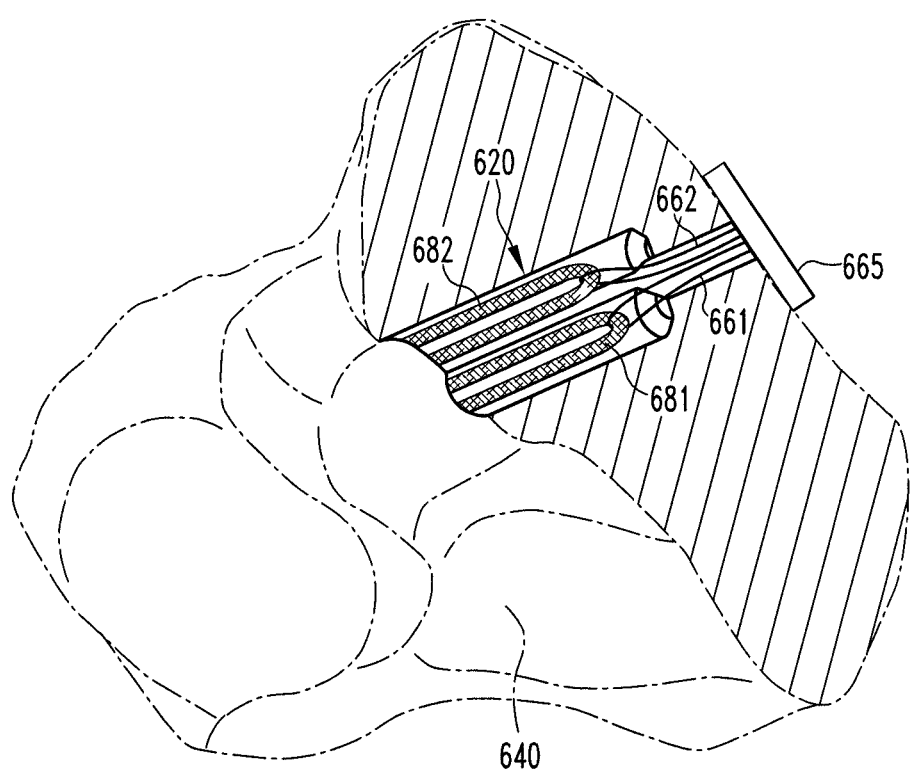
FIG. 6 is a is a cross-sectional schematic view of a graft attachment apparatus engaged with a surface of a bone, the graft attachment apparatus suspending a first graft and a second graft within a tunnel formed in the bone, according to embodiments disclosed herein.

Referring to FIG. 6, a cross-sectional schematic view of a graft attachment apparatus 665 engaged with a surface of a bone 640, the graft attachment apparatus 665 suspending a first graft 681 and a second graft 682 within a tunnel 620 formed in the bone 640, in accordance with embodiments disclosed herein, is shown. As shown, according to one or more aspects, the graft attachment apparatus 665, i.e., a fixation device, may be oriented on the surface of the bone 640 to prevent the graft attachment apparatus 665 from being disposed into the tunnel 620 formed in the bone 640, which may retain the graft attachment apparatus 665 on the surface of the bone 640. Further, as shown, a first suture 661 and a second suture 662 may be coupled to the graft attachment apparatus 665.

According to one or more aspects, the bone 640 may be a tibia and/or a femur. However, those having ordinary skill in the art will appreciate that the bone 640 may be any bone in a body, and may not be limited to only a tibia and/or a femur. For example, according to one or more aspects, the bone 640 may be a humerus.

As discussed above, each of the first suture loop 661 and the second suture loop 662 may be separately formed suture loops. Further, those having ordinary skill in the art will appreciate that the at least two suture loops 661, 662 may be formed from any material known in the art. For example, in one or more embodiments, each of the first suture loop 661 and the second suture loop 662 may be formed from a continuous loop of polyester, suture, or polyester closure tape.

Further, according to one or more aspects, the at least two separately formed suture loops 661, 662 may be different in length. In other words, a length of the first suture loop 661 may be different from a length of the second suture loop 662. In one or more embodiments, the first suture loop 661 may have a length of 15 mm, and the second suture loop 662 may have a length of 20 mm. However, as discussed above, those having ordinary skill in the art will appreciate that each of the first suture loop 661 and the second suture loop 662 may be of any length. According to one or more aspects, both the first suture loop 661 and the second suture loop 662 may have equal lengths.

According to one or more aspects, each of the two separately formed suture loops 661, 662 may be configured to be coupled, or attached, to separate grafts or ligaments, e.g., anteromedial (AM) and posterolateral (PL) fiber bundles. However, those having ordinary skill in the art will appreciate that each of the first suture loop 661 and the second suture loop 662 may be configured to be coupled, or attached, to any other grafts known in the art as well as any number of grafts known in the art.

For example, as shown, the first suture loop 661 is coupled to the first graft 681 and the second suture loop 662 is coupled to the second graft 682. Each of the first suture loop 661 and the second suture loop 662 may be coupled to the graft attachment apparatus 665, which may be engaged with a surface of the bone 640. As such, each of the first graft 681 and the second graft 682 may be suspended within the tunnel 620 formed in the bone 640 by the graft attachment apparatus 665 and the first suture 661 and the second suture 662.

As discussed above, it may be advantageous, for recovery purposes, to orient the first graft 681 and the second graft 682 within the tunnel 620 in a pre-determined orientation. For example, according to one or more aspects, it may be advantageous to place the first graft 681 near an anterior region, and medially, in the tibia, and close to the "over the top" position in the femur. In other words, according to one or more aspects, it may be advantageous, both anatomically and physiologically, to place the first graft 681 and the second graft 682 in a pre-determined orientation within the tunnel 620 by manipulating the graft attachment apparatus 665 to more closely reproduce the native ACL, without having to drill additional tunnels within the bone 640. According to one or more aspects, this may be accomplished by turning, twisting, or otherwise re-orienting the graft attachment apparatus 665 within the tunnel 620 such that the first graft 681 and the second graft 682 are aligned in the pre-determined orientation.

Advantageously, embodiments disclosed herein may provide a guide apparatus and a method of ligament reconstruction that may be used to allow a fixation device, coupled with at least two, separate grafts, to be utilized in a single bone tunnel. As such, multiple-bundle, e.g., double-bundle, ACL re-construction utilizing a single bone tunnel, e.g., a single ovoid femoral and/or tibial tunnel, may be possible, with the fixation of separate anteromedial and posterolateral grafts may be possible. Such type of ACL re-construction may improve the control of knee laxity compared to a standard, anatomic, single-bundle ACL re-construction, without the need for separate bone tunnels.

While embodiments have been described with respect to a limited number of embodiments, those skilled in the art, having benefit of this disclosure, will appreciate that other embodiments can be devised which do not depart from the scope of embodiments disclosed herein. Accordingly, the scope of embodiments disclosed herein should be limited only by the attached claims.

What is claimed is:

1. A method for ligament construction comprising:
   providing a guide configured to allow a drill to drill an oval-shaped tunnel within a bone;
   providing a fixation device having at least two separately-formed suture loops wherein a first graft and a second graft are coupled to the at least two suture loops;
   drilling an oval-shaped tunnel through a bone with the drill by drilling a central tunnel for receiving the guide, disposing a portion of the guide into the central tunnel, drilling a first tunnel, pivoting the guide, and then drilling at least a second tunnel;
   drawing the fixation device through the oval-shaped tunnel;
   orienting the first graft and the second graft within the oval-shaped tunnel; and
   securing the fixation device on an exterior surface of the bone.

2. The method of claim 1, wherein the guide comprises:
   a body having a proximal end, a distal end, a hole formed therethrough, and a central axis defined therethrough; and
   a projection member coupled to the distal end of the body.

3. The method claim 2, wherein drilling an oval-shaped tunnel through a bone with the drill further comprises:
   disposing the drill within a hole formed through the guide;
   drilling the first tunnel into the bone; and
   drilling the second tunnel into the bone, wherein the first tunnel overlaps the second tunnel.

4. The method of claim 3, wherein disposing at least a portion of the guide into the central tunnel formed in the bone comprises disposing at least a portion of the projection member of the guide into the central tunnel formed in the bone.

5. The method of claim 3, further comprising:
    pivoting the guide about the projection member between a first position and a second position.

6. The method of claim 1, wherein a lead suture is coupled to the fixation device.

7. the method of claim 6, wherein drawing the fixation device through the oval-shaped tunnel comprises drawing the fixation device through the oval-shaped tunnel with the lead suture.

8. The method of claim 6, wherein a flip suture is coupled to the fixation device.

9. The method of claim 1, further comprising:
    orienting the fixation device within the oval-shaped tunnel, wherein orienting the fixation device within the oval-shaped tunnel comprises substantially aligning a longitudinal axis of the fixation device with a longitudinal axis of the oval-shaped tunnel.

10. The method of claim 1, wherein securing the fixation device on an exterior surface of the bone comprises:
    re-orienting the fixation device such that a longitudinal axis of the fixation device is substantially perpendicular to a longitudinal axis of the oval-shaped tunnel.

11. The method of claim 10, wherein re-orienting the fixation device such that a longitudinal axis of the fixation device is substantially perpendicular to a longitudinal axis of the oval-shaped tunnel comprises:
    manipulating the flip suture to re-orient the fixation device on a surface of the bone.

\* \* \* \* \*